United States Patent [19]
Simon et al.

[11] Patent Number: 5,542,919
[45] Date of Patent: Aug. 6, 1996

[54] PERITONEAL DIALYSIS DEVICE

[75] Inventors: Wolfgang Simon, Schweinfurt; Günther Pototzky, Schonungen; Rolf Groos, Friedrichsdorf; Günter Schmidt, Haltern, all of Germany

[73] Assignee: Fresenius AG, Bad Homburg, Germany

[21] Appl. No.: 464,303

[22] Filed: Jun. 5, 1995

[30] Foreign Application Priority Data

Jun. 6, 1994 [DE] Germany .................. 44 21 126.0

[51] Int. Cl.$^6$ ............................................. A61M 1/00
[52] U.S. Cl. ........................ 604/29; 417/395; 604/67
[58] Field of Search .................... 604/29, 30, 67, 604/132, 141; 417/198.2, 205, 382, 395; 128/DIG. 12, DIG. 13

[56] References Cited

U.S. PATENT DOCUMENTS

| | | | |
|---|---|---|---|
| 3,709,222 | 1/1973 | DeVries | 128/213 |
| 4,096,859 | 6/1978 | Agarwal et al. | 128/213 |
| 4,267,040 | 5/1981 | Schäl | 210/104 |
| 4,381,003 | 4/1983 | Buoncristiani | 128/213 |
| 4,412,917 | 11/1983 | Ahjopalo | 210/104 |
| 4,618,343 | 10/1986 | Polaschegg | 604/29 |
| 4,770,769 | 9/1988 | Schael | 210/96.2 |
| 4,997,570 | 3/1991 | Polaschegg | 210/646 |
| 5,004,459 | 4/1991 | Peabody et al. | 604/29 |
| 5,141,493 | 8/1992 | Jacobson et al. | 604/29 |
| 5,269,811 | 12/1993 | Hayes et al. | 417/395 X |

FOREIGN PATENT DOCUMENTS

| | | |
|---|---|---|
| 149001 | 7/1985 | European Pat. Off. . |
| 2371931 | 6/1978 | France . |
| 2838414 | 10/1984 | Germany . |
| 8714464.6 | 3/1988 | Germany . |
| 3837498 | 5/1990 | Germany . |
| 4308586 | 11/1994 | Germany . |

*Primary Examiner*—Randall L. Green
*Assistant Examiner*—A. T. Nguyen
*Attorney, Agent, or Firm*—Marshall, O'Toole, Gerstein, Murray & Borun

[57] ABSTRACT

Peritoneal dialysis device (10) with a balancing chamber (28), which is divided into two balancing chamber halves (32 and 34) by a membrane (30), with an introduction line arrangement (16, 20, 22, 24), a discharge arrangement (22, 24, 20, 62), a catheter line arrangement (36, 38, 42), a valve arrangement (46–52), a pump arrangement (60, 108, 110) and a control unit (82), which switches the balancing chamber halves (32 and 34) in the filling or emptying operation with the aid of the valve arrangement (46–52).

The peritoneal dialysis device (10, 106) operates under pressure monitoring volumetrically in the filling phase and pressure-controlled in the emptying phase, and determines the volume of dialysis fluid introduced or discharged from the number of balancing chamber strokes and the ultrafiltration volume from the difference of these.

12 Claims, 2 Drawing Sheets

PERITONEAL DIALYSIS DEVICE

BACKGROUND OF THE INVENTION

The invention is concerned with a peritoneal dialysis device with a balancing arrangement with two chambers, each of which can be switched with a valve arrangement into a filling or emptying phase, with the peritoneal dialysis liquid source connected to the balancing arrangement through an inlet line, a catheter line that can be connected to the peritoneal catheter, starting from the balancing arrangement, a discharge line starting from the balancing arrangement, a pump arrangement for transporting fresh or used peritoneal dialysis fluid and a control unit for controlling the valve arrangement and the pump arrangement.

Devices for automated peritoneal dialysis, called "cycler" below, have the task to move peritoneal dialysis fluid in a defined amount and at a defined temperature into the peritoneal cavity of a patient with the aid of a permanent catheter and then to remove it again after a period of exposure, whereby the ultrafiltrate produced in the peritoneal cavity during the dialysis treatment is to be removed at the same time. This basic process is repeated at cyclic intervals corresponding to the particular clinical procedure and the individual requirements of the treatment.

The fluid should be administered in as short a time as possible in a predetermined amount and, after the exposure time, should be removed, again in as short a time as possible, whereby the amount removed must be determined more accurately so that a sufficiently accurate conclusion can be obtained about the balance and thus about the amount of ultrafiltrate produced by the body. During the inlet and outlet of the fluid, the patient must not be endangered and the way the patient feels must not be influenced adversely. It must also be determined accurately as to when the peritoneal cavity is sufficiently empty in order to start the next inlet.

Usually, the patient connects himself to such a cycler during at-home dialysis. The actual treatment then partially takes place during sleep, so that simple operation and absolute safety are indispensable. The function should not be influenced adversely by corpuscular components in the discharged fluid, which may occur, especially in the case of patients with inflammations. Finally, the fluid transfer must take place under absolutely sterile conditions because otherwise peritonitis may occur, which is sometimes life-threatening.

Already a number of peritoneal dialysis devices have become known, some of which are fully automatic, but fulfill the above requirements only partially.

A peritoneal dialysis device has become known from the Münchener Medizinischen Wochenzeitschrift (1972), p. 313, where a certain amount of peritoneal dialysis fluid by volume is administered to the patient. After the dialysis phase, this fluid is again removed from the patient and a volume balance must be set up. However, it is not obvious as to how the amount of ultrafiltration is to be determined.

An automatic peritoneal dialysis device has also become known from U.S. Pat. No. 3,709,222, which administers dialysis fluid to a patient with the aid of proportioning chambers in a time-dependent manner. Volumetric control of the transported fluid cannot be attained with this arrangement because the expandable chambers used there, for example, the backflow chambers, are used in connection with path-dependent sensors, so that accurate volumetric control is not provided.

Further peritoneal dialysis devices are described in U.S. Pat. No. 4,096,859, 4,412,917, 4,381,003, and 5,004,459. According to the first two US patents, weighing means are used which are difficult to handle and therefore do not come into consideration because the handling of the cycler must be as simple as possible. The devices according to the latter two US patents also have disadvantages, since these use peristaltic pumps, for which it is known that the transport rate depends on the inlet pressure. Since these inlet pressures vary greatly, depending on the type of transport, such pump arrangements have very large volumetric errors, so that one cannot use them in ultrafiltration control in peritoneal dialysis.

EP-A 149,001 describes a peritoneal dialysis device in which the dialysis fluid in an extracorporeal cycle is introduced into the patient through the semipermeable membrane of a filter through the catheter. Although this device operates partly controlled, partly regulated, it is too expensive and it is also difficult to operate, quite apart from the fact that the disposables used there are too expensive. The same applies to the disposable device known from DE-G 87 14 464.

Finally, exactly balancing systems are known for hemodialysis in which fresh and used dialysis fluids are constantly balanced against one another in a closed cycle in a balancing chamber.

SUMMARY OF THE INVENTION

Therefore, the task of the invention is to provide a peritoneal dialysis device of the type mentioned at the outset, which makes accurate volume determination of the introduced and removed peritoneal dialysis fluids possible in a simple and reliable manner.

The task is solved by the fact that the peritoneal dialysis device has a single balancing chamber which is separated into two balancing chamber halves by a movable liquid-impermeable membrane, whereby the balancing chamber halves are in flow-connection with the valve arrangements either to the source for the peritoneal dialysis fluid during inlet operation or to the discharge line during discharge operation and, on the other hand, with the catheter line, with a first pressure sensor being arranged in the catheter line, which gives a pressure-dependent signal that inactivates the control unit when a predetermined pressure value has been reached, and a device for determining the complete filling of the balancing chamber, the signal of which makes the control unit to switch the valve arrangement cyclically.

The peritoneal dialysis device has a balancing chamber that is divided into two halves by a movable, liquid-impermeable wall. The amount of liquid introduced into one half displaces the amount of fluid present in the other half in exact volumetric correspondence by displacement of the wall. As a result of this, the inlet and outlet volume can be determined with high accuracy, with an accuracy of one chamber volume (approx. 1% error), so that the ultrafiltered amount can also be determined accurately too. This results in better control of the treatment and consequently the dialysis treatment can be optimized. Otherwise, damage to the patient through over-filling can be reliably avoided by pressure control.

The filling and emptying can be carried out in the physiologically shortest time by monitoring the inlet and outlet pressure in a controlled manner. Thus, for example, a relative excess pressure or reduced pressure of 100 mbar can be monitored without any problems.

As a result of this, a defined treatment can be carried out largely independently of the position and movement of the patient, so that restrictions to the patient are saved. The accuracy and reliability of the system is independent of contaminants (blood, etc.).

A special advantage of the invention is the fact that the balancing chamber, including all the tube inlets, is designed as a nonaerated, disposable system with highly reliable sterility, all the parts being made advantageously of polymeric material. Such a balancing chamber is described, for example, in DE-A 41 16 178, but that is used for hemofiltration.

Furthermore, it is advantageous when this disposable system is present in the form of a compact cassette that is easy to handle, and this cassette has to be arranged on a correspondingly designed basic device before treatment. Then, this basic device contains the other operating parts, such as pumps, tube valves, pressure sensors and similar.

BRIEF DESCRIPTION OF THE DRAWINGS

The following are shown.

DETAILED DESCRIPTION OF THE DRAWINGS

Figure 1:
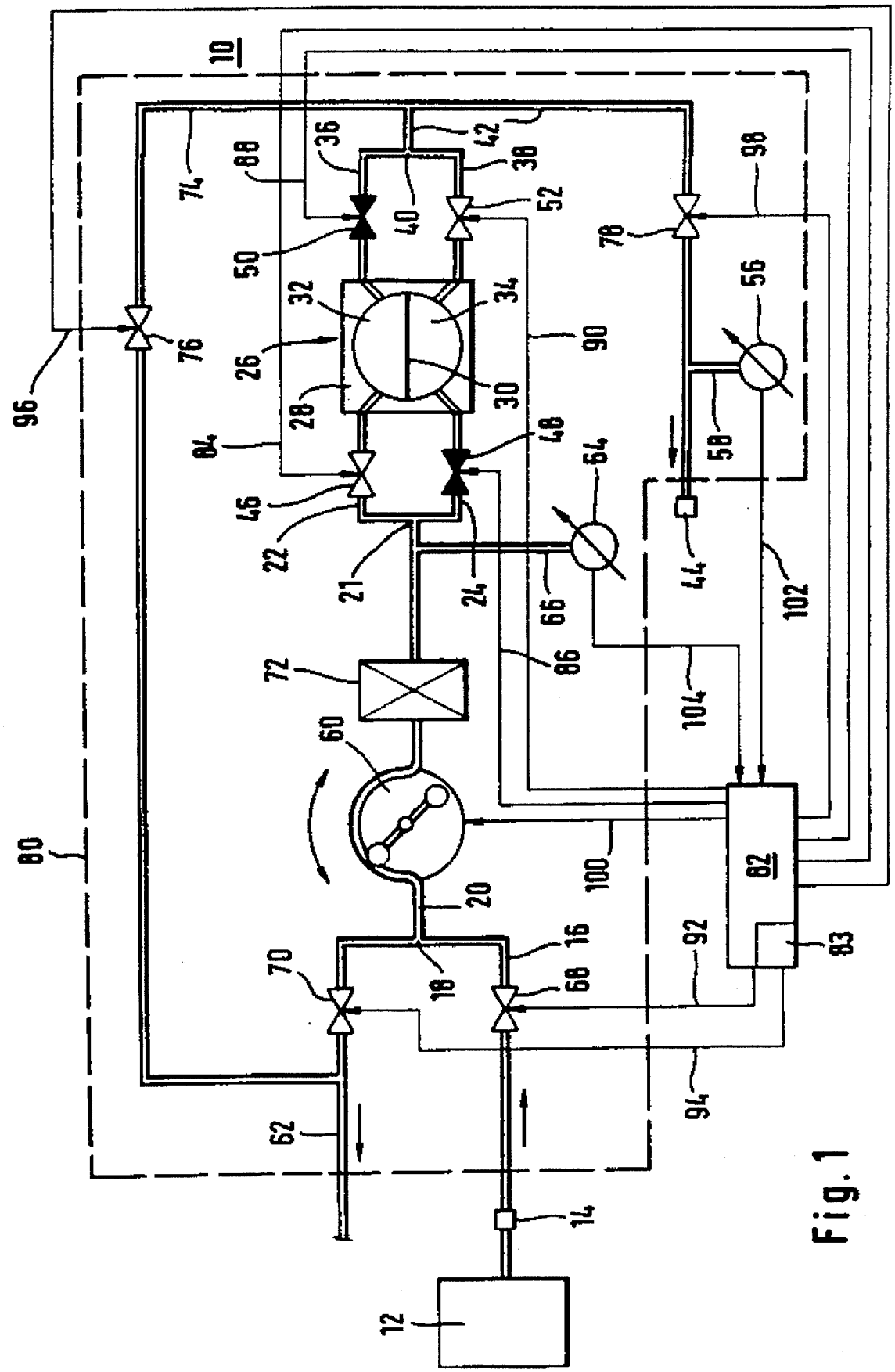
FIG. 1 is a first embodiment of a peritoneal dialysis device in schematic representation.

FIG. 1 shows a peritoneal dialysis device 10 schematically. This peritoneal dialysis device 10 has a source 12 for the peritoneal dialysis fluid, which usually consists of a number of plastic bags filled with a sterile peritoneal dialysis fluid. These bags are connected in a sterile manner to at least one inlet line 16 through a connector device 14. Otherwise, however, the peritoneal dialysis fluid can also be produced on-line from electrolyte concentrates and an osmotically-active substance (for example, glucose or glucose polymers) by mixing with water. Source 12 is to be understood as standing for such a device.

The inlet line 16 extends from source 12 or connector arrangement 14 to a branching point 18 and there it becomes a transporting line 20 which branches at its end 21 into a first balancing chamber line 22 and a second balancing chamber line 24.

Both lines 22 and 24 open into a balancing chamber 26.

The balancing chamber 26 consists essentially of a rigid balancing chamber housing 28, which is subdivided into a first balancing chamber half 32 and into a second balancing chamber half 34 by a mobile liquid-impermeable membrane 30. The two balancing chamber halves 32 and 34 form the actual balancing chamber 26, which has a predetermined constant volume (advantageously, about 20–30 mL).

As can be seen from FIG. 1, the first balancing chamber line 22 opens into the first balancing chamber half 32, while the second balancing chamber line 24 opens into the second balancing chamber half 34.

From the first balancing chamber half 32, a third balancing chamber line 36 starts and from the second balancing chamber 34, a fourth balancing chamber line 38 starts, which merge in a branching point 40.

A catheter line 42 extends from branching point 40; the end of the catheter line can be connected to a peritoneal dialysis catheter (not shown) through a further connector arrangement 44.

In the first, second, third and fourth balancing chamber line 22, 24, 36, and 38, the first, second, third and fourth valves are provided, respectively, the first and the fourth valve 46, 52, representing a first valve pair and the second and third valves 48, 50, shown darkened in the drawing, representing a second valve pair. According to the invention, the first and second valve pairs are activated in an opposite manner, that is, while the first valve pair is closed, the second valve pair is opened, and vice versa.

Furthermore, the catheter line 42 is connected to a pressure detector 56, namely, either directly at the periphery of the line or with the aid of a connecting line 58, which is connected to pressure detector 56 under sterile conditions. This pressure detector 56 is able to determine pressure differences of 0–200 mbar (reduced pressures or excess pressures) exactly.

According to the embodiment shown in FIG. 1, only one pump 60 is provided for inlet and outlet transport of the dialyzing fluids. This pump 60 is connected into transport line 20.

As can be seen from FIG. 1, fresh dialysis fluid is transported through inlet line 16 into transport line 20 in the clockwise direction, while the removal of used dialysis fluid occurs from transport line 20 into a discharge line 62 in the counterclockwise direction, the discharge line 62 starting from branching point 18 and opening into a discharge, which is not shown.

According to a first embodiment, between balancing chamber 26 and pump 60, in the region of transport line 20, a second pressure detector 64 is provided as a device for determining when the balancing chamber 26 is completely filled. The pressure detector is connected either directly to transport line 20 or is in pressure connection through a connecting line 66. As it is well-known, when the balancing chamber is filled, the pressure increases rapidly, so that the pressure increase can be used for switching the particular valve pairs 46, 52; 48, 50, optionally together with stopping the pump.

The first embodiment of a peritoneal dialysis device 10 shown in FIG. 1, which has only one pump 60, advantageously has a fifth valve 68 introduced into inlet line 16 and a sixth valve 70 introduced into discharge line 62, these also being activated in the opposite sense.

Furthermore, a heating device 72 is provided in the form of a heating bag, which, as shown in FIG. 1, is arranged advantageously between pump 70 and balancing chamber 26 in transport line 20. Such heating bags are known and serve to heat the peritoneal dialysis fluid to the body temperature of the patient. However, on the other hand, such a heating bag 72 can also be arranged in inlet line 16 upstream of the fifth valve 68.

For the purpose of deaeration or for pressure equalization, a deaeration line 74 leaves the catheter line 42 and opens into discharge line 62 downstream of the sixth valve 70. A seventh valve 76 is connected in deaeration line 74.

Finally, upstream of the first pressure sensor 56 and downstream of the branching point of the deaeration line 74, an eighth valve 78 can be provided in catheter line 42.

All the lines shown in FIG. 1, which are connected to balancing chamber 26, are made of polymeric materials, as are the balancing chamber 26 itself and heating bag 72. According to a further embodiment, all components are arranged in a predetermined position in a cassette 80 which is customarily also made of synthetic plastic shown in FIG. 1 by the dotted line. The valves again are designed advantageously as clamps that can be activated electrically, and which exert a clamping action on the elastic wall of the tubes as long as cassette 80 is inserted. Pressure sensors 56 and 64 also act advantageously by contacting the tube wall and apply the pressure inside the tubes by deforming the tubes. However, on the other hand, integrated, disposable sensors can also be used in the tubes.

In order to control the peritoneal dialysis device 10, a control unit 82 is provided, which is connected through control lines 84–98 with the first to the eighth valves 46–52, 68, 70, 76 and 78. Control line 82 is connected to pump 60 and ninth control line 100. It receives signals from the first and second pressure sensor 56 and 64, respectively, through signal lines 102 and 104.

The peritoneal dialysis device 10 shown in FIG. 1 is operated as follows:

First, fresh peritoneal dialysis fluid is made ready in source 12. The patient is connected through the peritoneal dialysis catheter to connection device 44. Then the peritoneal dialysis device 10 is activated and is set to inlet. After that, valve 68 in the inlet line 16 is opened, while valve 70 in the outlet line 62 remains closed. Pump 60 is switched to inlet operation and, at the same time, the heating for the heating bag is activated.

Then control line 82 switches the first and second valve pairs 46, 52 and 50, 48, respectively, in an alternating manner, as soon as the first or second balancing chamber half 32, 34, respectively, is filled. As a result of filling the balancing chambers 32 or 34, the pressure increases in inlet lines 20, 22, 24, which is determined with the aid of sensor 64 and is then used for triggering the switching signal.

Fresh dialysis fluid is introduced through lines 16, 20, 22 and 24 to the first balancing chamber 32 and to the second balancing chamber 34, respectively. During the filling of the complementary balancing chamber, the other balancing chamber half, which is completely filled, is displaced toward the patient through line 36 and 38 and the catheter line 42, as a result of displacement of the movable membrane 30. As a result of this, a substantially continuous transport of fluid to the patient is produced—a faster and more protective procedure.

Each switching signal thus corresponds to a displaced balancing chamber volume fraction of dialysis fluid. These switching signals are summated in control unit 82 and, at the end of the inlet phase, will give the absolute amount of introduced dialysis fluid by multiplication with the known balancing chamber volume.

With the aid of the first pressure sensor 56, the introduction pressure into the catheter line 42 is measured. A predetermined excess pressure is established in control unit 82 for the introduction phase, for example, +100 mbar, and this must not be exceeded. Thus, consequently, the pumping rate at pump 60 is controlled in such a way that this positive limiting pressure is not exceeded. As a result of this, filling is achieved in the shortest possible physiologically tolerable time, without any dangerous excess pressure situations occurring.

When switching the balancing chamber valves 46–52, not only the increase of pressure at the second pressure sensor 64 can be determined, but it can also be determined by the increase of the motor current of pump 60. It is expedient here to keep all balancing chamber valves 46–52 closed for a short time during switching, so that the overall balance is not disturbed. The process of progressing switching thus leads to a quasicontinuous flow of dialysis fluid through balancing chamber 26 and thus to the peritoneal catheter.

The inlet phase is completed when, upon reaching a predetermined amount of introduced dialysis fluid (which can be determined by the number of cycles) or preferably after exceeding a predetermined excess pressure at the first pressure sensor 56, optionally, at a smaller and smaller transportation rate, the control unit 82 is correspondingly activated.

At the end of the inlet phase, the eighth valve 78 is closed, so that upstream from it, all other parts, valves and pump 60 can be deactivated. If excess dialysis fluid or excess air is present in the catheter inlet, these fluids can be removed into the discharge through the deaeration line 74, whereby the seventh valve 76 is activated for this purpose. This operation is especially important when pressure equalization is to be created in catheter line 42, which usually occurs before closing valve 78.

The inlet phase is followed by the patient treatment phase, the duration of which is determined with a timing element 83 arranged within control unit 82.

After the completion of this peritoneal dialysis cycle, the peritoneal dialysis device 10 is switched to the discharge phase. For this purpose, first of all, valve 78 is opened. Similarly, valve pairs 46 and 52 as well as 48 and 50 are switched again alternatingly when the complete degree of filling of balancing chamber 26 is reached, which can be determined by the fact that a predetermined reduced pressure is exceeded, as detected at the second pressure sensor 64. The removal of the used dialysis fluid is done with the aid of pump 60, the direction of rotation of which is switched by control device 82 (counterclockwise).

After pump 60 is in the suction stage, now reduced pressure exists at pressure sensor 56, which is used to control the pump rate when a predetermined value is reached.

Furthermore, inlet valve 68 is closed and outlet valve 70 is opened. The deaeration valve 76 is closed during this phase.

Removal of used dialysis fluid is done under pressure control with the aid of the first pressure sensor 56, whereby a predetermined reduced pressure, for example, −100 mbar, must not be exceeded.

However, first, there is a slight excess pressure in the peritoneal cavity, so that used dialysis fluid can be removed at a relatively high removal rate. At the end of the removal process, the reduced pressure increases so that, when reaching the predetermined limiting value, the pump rate is reduced in a stepwise manner. Thus, a amount transported is reduced until the pump stops or a very small predetermined transportation rate is reached, or a balancing chamber cycle is completed in this phase.

This is a signal for the end of the emptying phase. Then, again, all balancing chamber strokes are summated and the total amount of removed dialysis fluid is determined. The difference between the introduced and removed amount of fluid then gives the amount of fluid that was removed from the patient by ultrafiltration.

At the end of this phase, the total arrangement is aerated against the surroundings, opening valve 76. All other aggregates are deactivated. Then valve 78 is closed.

After this the inlet phase is started again.

Figure 2:
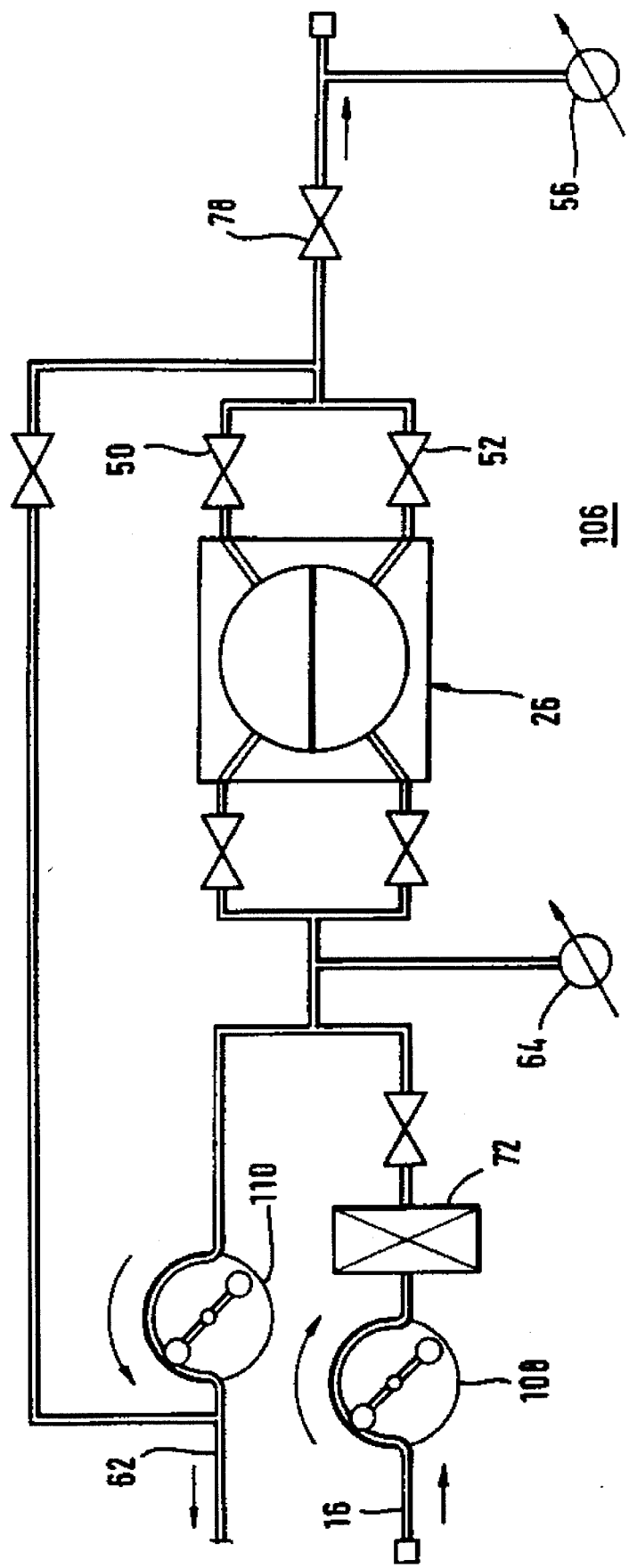
FIG. 2 is a second embodiment of a peritoneal dialysis device, also in schematic representation.

FIG. 2 is a second embodiment of a peritoneal dialysis device 106, the structure of which is highly similar to that of peritoneal dialysis device 10, according to FIG. 1. Therefore, the same reference numbers are used for the equivalent parts.

The second embodiment differs from the first embodiment only by the fact that, instead of a pump 60 that can be operated both-sided, two pumps are used. An inlet pump 108 as a peristaltic pump is provided in introduction line 16 upstream of valve 68, while a discharge pump 110 is provided in discharge line 62, also designed as a peristaltic roller pump.

It should be added that valves 68 and 70 according to the second embodiment do not necessarily have to be provided, if peristaltic pumps 108 and 110 with occluding action are used.

The embodiment according to FIG. 2 is operated in the same way as the embodiment according to FIG. 1. In the inlet phase, inlet pump 108 is activated while only the discharge pump 110 is activated during the discharge phase. Based on their occluding properties, when they are stopped, the two pumps 108 and 110 act as clamping valves and thus close the lines connected to them.

Advantageously, all valves are designed as clamping valves and can also be partially designed or switched in groups.

One or several temperature sensors are expedient in the tubing for controlling and monitoring the heating. An air detector can also be included between valve 78 and valves 50 and 52 to increase safety.

According to another advantageous embodiment, redundant pressure monitoring is carried out by the two pressure sensors 56 and 64, which are coupled hydraulically to one another through the lines and the balancing chamber 26. After treatment, the patient is disconnected from cassette 80, which is then discarded.

We claim:

1. Peritoneal dialysis device (10, 106) comprising (a) a balancing arrangement with two chambers (32, 34), which can be switched into a filling or emptying phase by a valve arrangement (46–52), (b) a peritoneal dialysis fluid source (12), which is connected to the balancing arrangement through an introduction line (16, 20, 22, 24), (c) a catheter line (42) that starts from the balancing arrangement and can be connected to a peritoneal catheter, (d) a discharge line (22, 24, 20, 62) starting from the balancing arrangement, (e) a pump arrangement (60, 108, 110) for transporting fresh or used peritoneal dialysis fluid, (f) a control unit (82) for controlling the valve arrangement (46–52) and the pump arrangement (60, 108, 110), (g) a single balancing chamber (26), which is separated through a movable liquid-impermeable membrane (30) into the two balancing chamber halves (32, 34), the balancing chamber halves (32, 34) being connected alternately through the valve arrangement (46–52) either with the source for the peritoneal dialysis fluid (12) in the introduction operation or to the discharge line in the removal operation, and, on the other hand, to catheter line (42) in the flow connection, (h) a first pressure sensor (56) arranged in the catheter line (42), wherein upon the pressure-dependent signal of this sensor, the control unit (82) inactivates the pump when a predetermined pressure valve is reached, and wherein a device is provided for determining the complete filling of the balancing chamber, upon the signal of which the control unit (82) switches the valve arrangement cyclically.

2. Peritoneal dialysis device according to claim 1, wherein that the control unit (82) controls the pump rate in the emptying phase so that the pressure will not go below a predetermined reduced pressure and wherein the pump arrangement (10, 110) is turned off upon reaching a predetermined minimum pump rate, optionally at the end of the balancing chamber stroke, that lies directly before reaching this predetermined minimum pump rate.

3. Peritoneal dialysis device according to claim 1, wherein that the control unit (82) ends the filling operation by turning off the pump arrangement (60, 108) and switching the balancing arrangement (46–52) when a predetermined volume of peritoneal dialysis fluid had been introduced.

4. Peritoneal dialysis device according to claim 1, wherein that, both at the end of the filling phase, as well as at the end of the emptying phase, the control unit (82) determines the volume of peritoneal dialysis fluid transported through the balancing chamber (26) based on the number of switching cycles of the valve arrangement (46–52) and based on the known inside volume of the balancing chamber (26) and determines the particular ultrafiltration volume from the difference of the used and fresh dialysis fluid volume.

5. Peritoneal dialysis device according to claim 1, further comprising an inlet line (14) that goes from the dialysis fluid source (12) to a first branching point (18), a discharge line (62), which leaves from the branching point (18) and opens into a discharge, a transport line (20), which leaves from the first branching point (18) and the end of which branches into a first balancing chamber line (22) and into a second balancing chamber line (24), whereby the first balancing chamber line (22) is connected to the first balancing chamber half (32) and the second balancing chamber line (24) is connected with the second balancing chamber half (34) in flow connection, a third balancing chamber line (36), leaving from the first balancing chamber half (32) and a fourth balancing chamber line (38), leaving from the second balancing chamber half (34), each of which open into a second connection point (40) from which a catheter line (42) leaves, the end of which can be connected to a peritoneal catheter, and a first, second, third and fourth valve (46–52) which are included in the first, second, third, and fourth balancing chamber lines (22, 24, 36, 38).

6. Peritoneal dialysis device according to claim 1, wherein that a peristaltic pump (60), which can be operated on both sides, is arranged in the transport line (20) and that the inlet line (16) has a seventh valve (68), which is opened in the inlet phase and the discharge line (62) has an eighth valve, which is opened in the discharge phase.

7. Peritoneal dialysis device according to claim 1, wherein an inlet pump (108) is provided in the inlet line (16) and a discharge pump (110) is disposed in the discharge line (62).

8. Peritoneal dialysis device according to claim 1, wherein the device for the determination of the complete filling of the balancing chamber (26) is a second pressure sensor (64), which is connected to the transport line (20).

9. Peritoneal dialysis device according to claim 1, wherein a fifth valve (78) is disposed in the catheter line (42).

10. Peritoneal dialysis device according to claim 9, wherein between the second connecting point (40) and the fifth valve (78), a bypass line (74) starts from the catheter line (52), and a sixth valve (76) is connected for aerating the catheter line (42), its end opening into the discharge line (62).

11. Disposable tubing system for the peritoneal dialysis device according to claim 1, having a balancing chamber (26), which is divided into two balancing chamber halves (32, 34) through a movable liquid-impermeable membrane (30), a balancing chamber line (22), which leaves from the first balancing chamber half (32) and a second balancing chamber line (24), which leaves from the second balancing chamber half (34), a transporting line (20), the first end of which is combined with the ends of the first balancing chamber line (22) and of the second balancing chamber line (24) and a second end of which branches off into an introduction line (16) which is suitable to be connected to a source (12) for peritoneal dialysis fluid, and into a discharge line (62), a third balancing chamber line (36), which leaves from the first balancing chamber half (32) and a fourth balancing chamber line (38), which leaves from the second balancing chamber half (34), and a catheter line (42), the first end of which is connected to the ends of the balancing chamber lines (36) and (38) and the second end of which is suitable to be connected to a peritoneal catheter.

12. System according to claim 11, wherein that a bypass line (74) branches off from the catheter line (42), this bypass being connected to the discharge line (62).

* * * * *